(12) United States Patent
Overes et al.

(10) Patent No.: US 9,925,053 B2
(45) Date of Patent: Mar. 27, 2018

(54) JOINT IMPLANT

(71) Applicant: 41medical AG, Bettlach (CH)

(72) Inventors: Tom Overes, Langendorf (CH); Robert Frigg, Bettlach (CH)

(73) Assignee: 41Hemiverse AG, Bettlach (CH)

( * ) Notice: Subject to any disclaimer, the term of this patent is extended or adjusted under 35 U.S.C. 154(b) by 0 days.

(21) Appl. No.: 15/029,237

(22) PCT Filed: Jul. 24, 2014

(86) PCT No.: PCT/CH2014/000114
§ 371 (c)(1),
(2) Date: Apr. 13, 2016

(87) PCT Pub. No.: WO2015/051471
PCT Pub. Date: Apr. 16, 2015

(65) Prior Publication Data
US 2016/0235539 A1 Aug. 18, 2016

(30) Foreign Application Priority Data
Oct. 13, 2013 (CH) ...................................... 1746/13

(51) Int. Cl.
*A61F 2/30* (2006.01)
*A61F 2/32* (2006.01)
(Continued)

(52) U.S. Cl.
CPC .............. *A61F 2/4014* (2013.01); *A61F 2/32* (2013.01); *A61F 2/34* (2013.01); *A61F 2/36* (2013.01); *A61F 2/40* (2013.01); *A61F 2/4081* (2013.01); *A61F 2002/30028* (2013.01); *A61F 2002/30225* (2013.01); *A61F 2002/30332* (2013.01);
(Continued)

(58) Field of Classification Search
CPC ............ A61F 2/4014; A61F 2002/4029; A61F 2002/4033; A61F 2002/4037; A61F 2002/404–2002/4055; A61F 2/4059; A61F 2002/2825–2002/2832;
(Continued)

(56) References Cited

U.S. PATENT DOCUMENTS 3,837,008 A 9/1974 Bahler et al.
3,869,730 A 3/1975 Skobel
(Continued)

FOREIGN PATENT DOCUMENTS

DE 102006041551 A1 11/2007
EP 1004283 A2 5/2000
(Continued)

*Primary Examiner* — Alvin Stewart
(74) *Attorney, Agent, or Firm* — MU P.C.

(57) ABSTRACT

The present application relates to an artificial joint implant comprising a first element with a socket and a second element with a ball head. The socket is at least hemispherical and said ball head is inserted in said socket such as to form a ball-and-socket connection between said first element and said second element. Movement of said ball head in said socket is restricted in at least one degree of freedom by means of a at least one protrusion engaged in a at least one groove, wherein said at least one protrusion is provided on said socket and said at least one groove is provided on said ball head or vice versa.

8 Claims, 5 Drawing Sheets

(51) Int. Cl.
*A61F 2/40* (2006.01)
*A61F 2/34* (2006.01)
*A61F 2/36* (2006.01)

(52) U.S. Cl.
CPC ............... *A61F 2002/30364* (2013.01); *A61F 2002/30367* (2013.01); *A61F 2002/30616* (2013.01); *A61F 2002/30635* (2013.01); *A61F 2002/30662* (2013.01); *A61F 2002/30663* (2013.01); *A61F 2002/30932* (2013.01); *A61F 2002/30937* (2013.01); *A61F 2002/3617* (2013.01); *A61F 2002/4018* (2013.01); *A61F 2002/4022* (2013.01); *A61F 2002/4029* (2013.01); *A61F 2002/4085* (2013.01); *A61F 2002/4088* (2013.01); *A61F 2002/4096* (2013.01); *A61F 2230/0093* (2013.01); *A61F 2230/0095* (2013.01)

(58) Field of Classification Search
CPC .................. A61F 2002/30378; A61F 2002/30649–2002/30652
USPC ........... 623/19.11–19.14, 22.4, 22.45, 22.46, 623/22.42, 22.15, 22.18
See application file for complete search history.

(56) References Cited

U.S. PATENT DOCUMENTS

| | | | | |
|---|---|---|---|---|
| 3,903,549 A * | 9/1975 | Deyerle | A61F 2/34 | 606/309 |
| 3,979,778 A | 9/1976 | Stroot | | |
| 4,003,096 A | 1/1977 | Frey | | |
| 4,040,130 A * | 8/1977 | Laure | A61F 2/4261 | 623/21.13 |
| 4,279,041 A * | 7/1981 | Buchholz | A61F 2/32 | 403/123 |
| 4,678,472 A * | 7/1987 | Noiles | A61F 2/32 | 623/23.4 |
| 4,950,299 A * | 8/1990 | Noiles | A61F 2/32 | 623/22.18 |
| 4,957,510 A * | 9/1990 | Cremascoli | A61F 2/3662 | 623/22.46 |
| 4,960,427 A * | 10/1990 | Noiles | A61F 2/32 | 623/22.18 |
| 5,171,285 A * | 12/1992 | Broderick | A61F 2/34 | 623/22.25 |
| 5,314,485 A * | 5/1994 | Judet | A61F 2/4261 | 623/21.13 |
| 5,702,457 A * | 12/1997 | Walch | A61F 2/4014 | 623/19.13 |
| 5,888,207 A * | 3/1999 | Nieder | A61F 2/32 | 623/23.15 |
| 5,910,171 A * | 6/1999 | Kummer | A61F 2/4014 | 623/18.11 |
| 6,042,611 A * | 3/2000 | Noiles | A61F 2/34 | 623/22.21 |
| 6,083,263 A * | 7/2000 | Draenert | A61F 2/3609 | 623/22.46 |
| 6,197,062 B1 * | 3/2001 | Fenlin | A61F 2/4014 | 623/19.12 |
| 6,197,063 B1 * | 3/2001 | Dews | A61F 2/4014 | 623/19.14 |
| 6,676,705 B1 * | 1/2004 | Wolf | A61F 2/4014 | 623/19.14 |
| 6,719,799 B1 * | 4/2004 | Kropf | A61F 2/4014 | 623/19.12 |
| 6,749,637 B1 * | 6/2004 | Bahler | A61F 2/4014 | 623/19.11 |
| 7,011,686 B2 * | 3/2006 | Ball | A61F 2/4014 | 623/19.14 |
| 7,097,663 B1 * | 8/2006 | Nicol | A61F 2/4014 | 623/19.12 |
| 7,108,720 B2 * | 9/2006 | Hanes | A61F 2/32 | 623/22.11 |
| 7,135,044 B2 * | 11/2006 | Bassik | A61F 2/36 | 623/22.42 |
| 7,238,207 B2 * | 7/2007 | Blatter | A61F 2/4014 | 623/19.14 |
| 7,335,231 B2 * | 2/2008 | McLean | A61F 2/32 | 623/22.15 |
| 7,393,362 B2 * | 7/2008 | Cruchet | A61F 2/32 | 623/22.18 |
| 7,455,694 B2 * | 11/2008 | Epaules | A61F 2/32 | 623/22.15 |
| 7,615,080 B2 * | 11/2009 | Ondrla | A61F 2/4014 | 623/19.11 |
| 7,776,098 B2 * | 8/2010 | Murphy | A61F 2/3609 | 623/22.42 |
| 8,002,838 B2 * | 8/2011 | Klotz | A61F 2/4014 | 623/19.14 |
| 8,062,376 B2 * | 11/2011 | Shultz | A61F 2/40 | 623/19.11 |
| 8,123,814 B2 * | 2/2012 | Meridew | A61F 2/30724 | 623/22.19 |
| 8,357,204 B2 * | 1/2013 | Ragbir | A61F 2/3609 | 623/23.15 |
| 8,398,718 B2 * | 3/2013 | Richardson | A61F 2/34 | 623/22.11 |
| 8,454,702 B2 * | 6/2013 | Smits | | 623/19.11 |
| 8,663,333 B2 * | 3/2014 | Metcalfe | A61F 2/4014 | 623/19.11 |
| 8,906,102 B2 * | 12/2014 | Viscardi | A61F 2/4014 | 623/19.11 |
| 2002/0143402 A1 | 10/2002 | Steinberg | | |
| 2003/0074079 A1 * | 4/2003 | McTighe | A61F 2/30767 | 623/22.42 |
| 2003/0171817 A1 * | 9/2003 | Rambert | A61F 2/32 | 623/22.17 |
| 2003/0233146 A1 | 12/2003 | Grinberg et al. | | |
| 2004/0143335 A1 * | 7/2004 | Dews | A61F 2/4014 | 623/19.14 |
| 2005/0203634 A1 * | 9/2005 | Bassik | A61F 2/36 | 623/22.42 |
| 2005/0228502 A1 * | 10/2005 | Deloge | A61F 2/32 | 623/22.18 |
| 2006/0079963 A1 | 4/2006 | Hansen | | |
| 2006/0259148 A1 * | 11/2006 | Bar-Ziv | A61F 2/30767 | 623/19.14 |
| 2007/0043448 A1 * | 2/2007 | Murray | A61F 2/30767 | 623/22.46 |
| 2007/0112430 A1 * | 5/2007 | Simmen | A61F 2/40 | 623/19.14 |
| 2007/0173945 A1 * | 7/2007 | Wiley | A61F 2/30734 | 623/19.13 |
| 2008/0091274 A1 * | 4/2008 | Murphy | A61F 2/3609 | 623/22.42 |
| 2008/0140210 A1 * | 6/2008 | Doubler | A61F 2/4059 | 623/19.14 |
| 2008/0140211 A1 | 6/2008 | Doubler et al. | | |
| 2008/0281430 A1 * | 11/2008 | Kelman | A61F 2/30734 | 623/23.23 |
| 2009/0062923 A1 | 3/2009 | Swanson | | |
| 2009/0192621 A1 | 7/2009 | Winslow et al. | | |
| 2009/0281630 A1 * | 11/2009 | Delince | A61F 2/40 | 623/19.13 |
| 2010/0100193 A1 * | 4/2010 | White | A61F 2/46 | 623/22.43 |
| 2010/0211178 A1 * | 8/2010 | Nogarin | A61F 2/40 | 623/19.14 |
| 2010/0241239 A1 * | 9/2010 | Smith | A61B 17/1668 | 623/22.42 |
| 2011/0009976 A1 * | 1/2011 | Cruchet | A61B 17/1668 | 623/22.46 |
| 2011/0035021 A1 * | 2/2011 | Bergin | A61F 2/30734 | 623/22.42 |
| 2012/0004733 A1 * | 1/2012 | Hodorek | A61F 2/40 | 623/19.11 |

(56) References Cited

U.S. PATENT DOCUMENTS

| | | | |
|---|---|---|---|
| 2012/0172992 A1* | 7/2012 | Fockens | A61F 2/4059 623/19.13 |
| 2012/0179262 A1* | 7/2012 | Metcalfe | A61F 2/4014 623/19.14 |
| 2013/0066433 A1* | 3/2013 | Veronesi | A61F 2/4081 623/19.13 |
| 2014/0107791 A1* | 4/2014 | Isch | A61F 2/4014 623/19.14 |
| 2014/0236304 A1* | 8/2014 | Hodorek | A61B 17/1778 623/19.14 |
| 2015/0039096 A1* | 2/2015 | McTighe | A61F 2/30767 623/23.35 |
| 2016/0113645 A1* | 4/2016 | Hardy | A61B 17/0401 623/19.14 |
| 2016/0166393 A1* | 6/2016 | Visser | A61B 17/68 623/19.14 |
| 2016/0193049 A1* | 7/2016 | McTigue | A61F 2/30767 623/19.14 |
| 2016/0235539 A1* | 8/2016 | Overes | A61F 2/40 |
| 2016/0256288 A1* | 9/2016 | Overes | A61F 2/40 |

FOREIGN PATENT DOCUMENTS

| | | | |
|---|---|---|---|
| EP | 1314407 | A1 | 5/2003 |
| FR | 2314702 | A1 | 1/1977 |
| WO | 0176511 | A1 | 10/2001 |
| WO | 2008000928 | A2 | 1/2008 |
| WO | 2008026135 | A1 | 3/2008 |
| WO | 2010105073 | A1 | 9/2010 |
| WO | 2011006852 | A1 | 1/2011 |

* cited by examiner

JOINT IMPLANT

TECHNICAL FIELD

The invention relates to a joint implant for artificial joints comprising two elements connected by a ball-and-socket connection, said ball-and-socket connection having at least one blocked degree of freedom.

BACKGROUND ART

Many different types of implants for artificial joints are known in the prior art. Specifically, joint implants having a ball-and-socket type are used for hip and shoulder implants. However, implants of the ball-and-socket type may also be used in condyloid joints, such as the radiocarpal joint of the wrist, metacarpophalangeal joints of the hand and metatarsophalangeal joints of the foot.

In certain types of implants, notably the radiocarpal, metacarpophalangeal and metatarsophalangeal joints at least one degree of freedom of movement of a ball-and-socket joint has to be restricted such as to mimic the function of the natural joint. Further, in certain circumstances, it may also be beneficial to limit the degree of freedom of movement of a ball-and-socket joint in artificial hip or shoulder implants.

WO2010/105073 relates to a reverse shoulder assembly. In one example, a reverse shoulder assembly may be provided such that the reverse shoulder assembly alters the abduction force created by a patient's deltoid to a forward flexion force. In one example, a reverse shoulder assembly may be provided such that the reverse shoulder assembly alters the abduction force created by a patient's deltoid to an external rotation force. In one example, a reverse shoulder assembly may be provided such that the reverse shoulder assembly alters the abduction force created by a patient's deltoid to an external rotation force and a forward flexion force.

SUMMARY OF THE INVENTION

It is the object of the invention to create a joint implant which allows limiting a movement of a ball-and-socket connection in at least one degree of freedom.

The solution of the invention is specified by the features of claim 1. According to the invention a joint implant comprises a first element with a socket and a second element with a ball head. The socket is at least hemispherical and said ball head is inserted in said socket such as to form a ball-and-socket connection between said first element and said second element. Movement of said ball head in said socket is restricted in at least one degree of freedom by means of at least one protrusion engaged in at least one groove. Thereby, said at least one protrusion is provided on said socket and said at least one groove is provided on said ball head or vice versa. Said first element further comprises an inlay rotatably coupled to a base portion around a first axis of rotation, wherein said at least one protrusion and said at least one groove are arranged to block at least a rotational movement of said ball-and-socket connection in a second axis of rotation which is essentially parallel to said first axis of rotation.

By provision of a protrusion and a groove a very simple yet effective restriction of the freedom of movement of the ball-and-socket connection is realized. Further, the inventive joint implant is very simple to assemble and features no additional parts which need to be fastened to the bones of a patient, hence allowing a quick and simple implantation in a patient. Further, ball-and-socket connections have a high congruency and exhibit excellent wear characteristics. Therefore, the same freedom of motion as a joint including two hinge axes with much better wear characteristics and less parts is achieved. The proposed configuration also allows offsetting the centre of rotation around said first axis. Preferably, the socket is located on an eccentric position on said inlay. Further, the socket may also be spaced from said inlay by means of a shaft or stem. Hence, different variations of the offset of the centre of rotation may be realized.

The first element and the second element may be shaped and sized according to the intended use of the joint implant. For example, the inventive joint implant may be used for hip replacement. In this case the first element may be formed as hemispherical acetabular cup. Accordingly, the second element featuring the ball head is formed as femoral component to be inserted in a patient's femur. Various embodiments of artificial acetabular cups and femoral components are known to a skilled person.

Further, as a second non-limiting example, the joint implant according to the present invention may be used for shoulder replacement. In this case, the first element is shaped as a glenoid disc to be inserted into the glenoid cavity of a patient. Accordingly, the second element is provided in the form of a humeral shaft to be inserted in the patient's humerus.

The present invention is not restricted to a specific shape, size or type of said first and said second elements but may rather be used in connection with various different types of artificial joints. For example, a joint implant according to the present invention may also be used to replace an elbow, knee, radiocarpal joint, metacarpophalangeal joint or metatarsophalangeal joint. In each of these exemplary uses, the first and the second element are shaped and sized to be implanted in the corresponding anatomical location of a patient.

Ball-and-socket type connections are known to a skilled person. Basically, a ball head shaped portion is inserted in a corresponding socket. Usually, a ball-and-socket type connection allows the ball head to rotate around three different axes within said socket. I.e. the ball head has three rotational degrees of freedom to move relative to the socket. Preferably, the socket is sized such that the ball head snugly fits within the socket, hence only allowing rotational movements of the ball head within the socket. However, in certain circumstances, the socket may be shaped such as to allow a limited translation of the ball head within the socket. In such a circumstance, the ball head will of course have more degrees of freedom. E.g. if translation is allowed in one direction for a limited distance, the ball head will have one translational degree of freedom and three rotational degrees of freedom, totalling four degrees of freedom.

The term "degree of freedom" as used in the present description is understood to encompass rotational movement around an axis of rotation as well as a translational movement along a line of travel.

By having an engagement of the at least one protrusion within the at least one groove the ball head is restricted from making a movement in a direction which would urge the protrusion out of the groove. Hence, only movements which allow the protrusion to move within the groove remain possible. The groove may therefore be considered a kind of guideway for the movements of the ball head within the socket.

The protrusion may be provided in the ball head. Hence, the groove will be provided in the socket. Alternatively, the protrusion may be located in the socket. In this case the groove is located in the ball head. As long as at least one protrusion engaged in at least one groove is provided, it is irrelevant whether the at least one groove or the at least one protrusion is located in said socket or in said ball head.

Preferably, the first element and/or the second element are provided as monobloc structures which preferably include surfaces enhanced for bone ingrowth, e.g. by application of a coating.

Preferably, said at least one groove is positioned along a great circle of said ball head or said socket. Provision of the groove along a great circle allows limiting the movement of the ball head within the socket along a first rotational axis intersecting the centre of the socket. However, as the at least one protrusion may glide along and rotate within said at least one groove, rotation about the two remaining axes of rotation, which are both orthogonal to said first rotational axis remains possible for said ball-and-socket connection.

Preferably, said at least one groove has a width which is equal to or larger than a width of said at least one protrusion. This allows the at least one protrusion to rotate and slide within said at least one groove.

In an embodiment, the width of said at least one groove is larger than the width of said at least one protrusion. Hence, the movement of the ball head in the at least one restricted degree of freedom is still possible, albeit only in a limited manner. This allows providing a joint implant having full motion capacity in all degrees of freedom except in the restricted degree of freedom, where only a limited range of motion is available. For example, this may allow for a limited "wobbling-type" motion, i.e. a motion with play in the restricted degree of freedom, for example to reduce the incidence of damage to the joint or surrounding tissue when an external force is exerted in the direction of the restricted degree of freedom.

Such as to still impair the motion in the restricted degree of freedom, the width of the at least one groove is not much larger than the width of the at least one protrusion. Typically, the width of the at least one groove will be between 100% and 125% of the width of the at least one protrusion. In the case where the at least one protrusion is round or oval, the width is understood to correspond to the diameter or the largest diameter of the protrusion.

Preferably, the at least one protrusion is cylindrical or hemispherical in shape. Such a shape allows unhindered movement of the at least one protrusion within said at least one groove.

Alternatively, said at least one protrusion may also be in the shape of a cuboid. However, with a cuboid shape, rotation of said at least one protrusion within said at least one groove may be hindered by jamming of edges or tips of the at least one protrusion with side walls of said at least one groove. Hence, by providing the at least one protrusion in the shape of a cuboid, it may be possible to restrict the movement of the ball-and-socket connection in a further degree of freedom, as side walls of the cuboid protrusion will engage with side walls of the groove thereby hindering a rotation of the at least one protrusion in said at least one groove.

Preferably, said at least one groove is provided on said socket and spans only a portion of the distance between the edge and the apex of said socket. Hence, movement of the at least one protrusion may be partially restricted in a second degree of freedom. This allows providing a joint implant where the motion of the ball-and-socket connection between the first element and the second element mimics a natural joint including any movement constraints. E.g. the joint implant may be provided such that the rotation of the ball head within the socket around one axis may be restricted to different maximal rotational angles depending on the direction of the rotation.

Preferably, said ball head is in the form of a dome or of a spherical segment. As such forms present at least one substantially flat portion, the second element may be provided in a great variety of shapes. Further, the substantially flat portion may comprise anchoring points for further implant components. This e.g. allows to use the inventive joint implant in a modular system, where a patient specific adaptation of the implant is made possible by providing different sizes of components attachable to the second element, such as for example stems of different lengths or diameters.

Preferably, said at least one groove is provided on said ball head, wherein said at least one groove spans only a portion of the distance between a circumferential edge and the apex of said dome or only a portion between two circumferential edges of said spherical segment.

In this way, movement of the at least one protrusion may be partially restricted in a second degree of freedom in the case where the at least one groove is arranged on the ball head. Preferably, the at least one protrusion has a central axis which is oriented such as to intersect the centre of the socket or ball-head, i.e. the at least one protrusion points towards said centre. Alternatively, the central axis may also be oriented such as not to intersect said centre, this enabling joint implants having an eccentrical centre of rotation.

Further, the ball-head is preferably locked within the socket such as to avoid any disassembly of the ball-and socket joint. This locking is preferably enabled by a form-fit engagement of the ball-head within the socket, e.g. by providing an opening to the socket which is smaller than the dimension of the ball-head once inserted and oriented in the correct direction. For example, the ball-head may be configured as dome having a defined largest circumference and a defined height. Typically, the largest circumference corresponds to the circumference of a great circle of the ball head. The socket is configured to feature an opening having dimensions which are larger than the height of the ball-head but smaller than the largest circumference. Therefore, the ball-head may only be inserted transversally into said socket. After a re-orientation of the ball head, the disassembly of the ball-and-socket connection is prevented since the largest circumference of the ball-head does not fit through the opening of the socket.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

DETAILED DESCRIPTION OF EMBODIMENTS OF THE INVENTION

Figure 1:
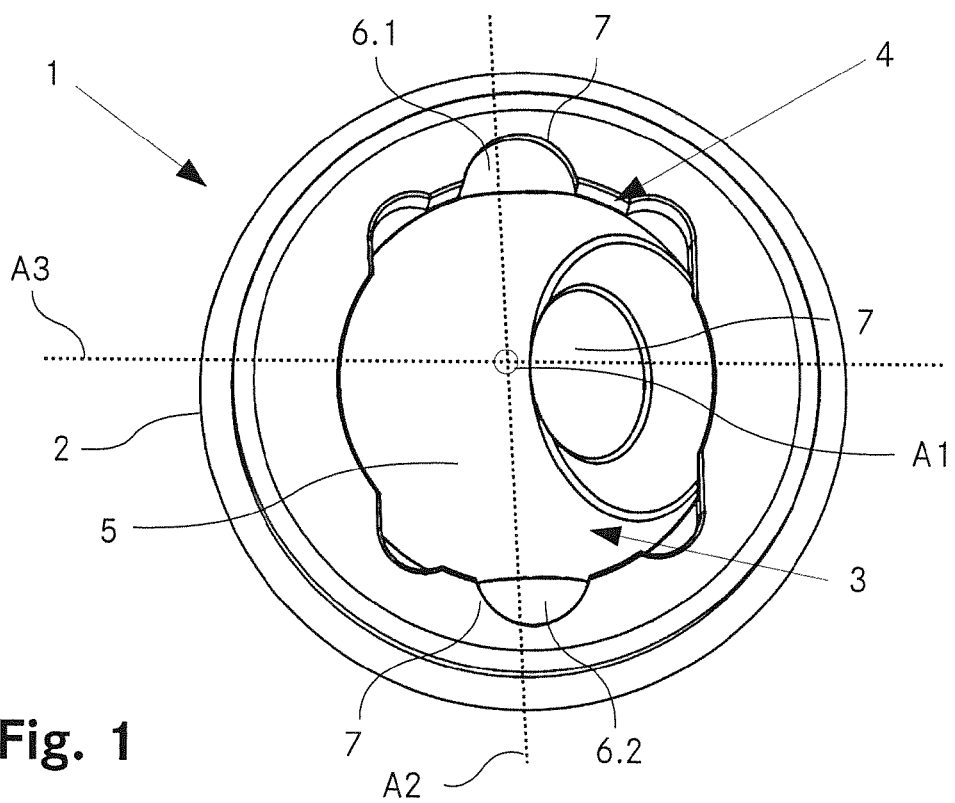
FIG. 1 An example joint implant according to the present invention.

FIG. 1 shows an exemplary joint implant 1 according to the present invention. The joint implant 1 comprises a first element 2 with a hemispherical socket 4. Further, the joint implant 1 comprises a second element 3 including a ball head 5. The ball head 5 is arranged within the socket 4 thus forming a ball-and-socket connection.

In the exemplary embodiment shown, the second element 3 comprises the ball head 5 as well as a connection portion 20 in the form of a hole, e.g. including a thread. Alternatively, the connection portion 20 may be configured as morse taper. Further components, such as a shaft or stem may be connected with the second element 3 by means of the connection portion 20. In the shown embodiment the ball head 5 is provided in the form of a dome.

The hemispherical socket 4 includes a groove 7 into which two protrusions 6.1, 6.2 provided on said ball head 5 are engaged. The groove 7 as well as the protrusions 6.1, 6.2 have a matching hemispherical shape. Without provision of the groove 7 and the protrusions 6.1, 6.2 the ball head 3 would be able to rotate freely around three axes of rotation A1, A2, A3 within the socket. It has to be noted that a first axis A1 is oriented parallel to the viewing direction when looking at the figure. However, the engagement of the two protrusions 6.1, 6.2 into the groove 7 restricts rotational movement of the ball head 3 around the first axis A1, as the two protrusions 6.1, 6.2 are form-fittingly engaged within the groove 7. Hence, the two protrusions 6.1, 6.2 engaged within the groove 7 results in a movement restriction of the joint implant 1 in one degree of freedom. In the shown embodiment, the groove 7 has the same shape and width as the two protrusions 6.1, 6.2, hence any movement around the first rotation axis A1 is prevented. Alternatively, the groove 7 may have a width which is slightly larger than the width of the two protrusions 6.1, 6.2. With such an alternative embodiment, the ball head 3 would be able to carry out small movements around the first axis of rotation A1, hence enabling a limited "wobbling" of the ball head 3 within the socket 4 around the third axis of rotation A1.

Rotational movement of the ball head 3 around a third axis of rotation A3 is enabled by a sliding motion of the two protrusions 6.1, 6.2 within the groove 7 and rotational movement around a second axis of rotation A2 by a rotation of the two protrusions 6.1, 6.2 within the groove 7.

Figure 2:
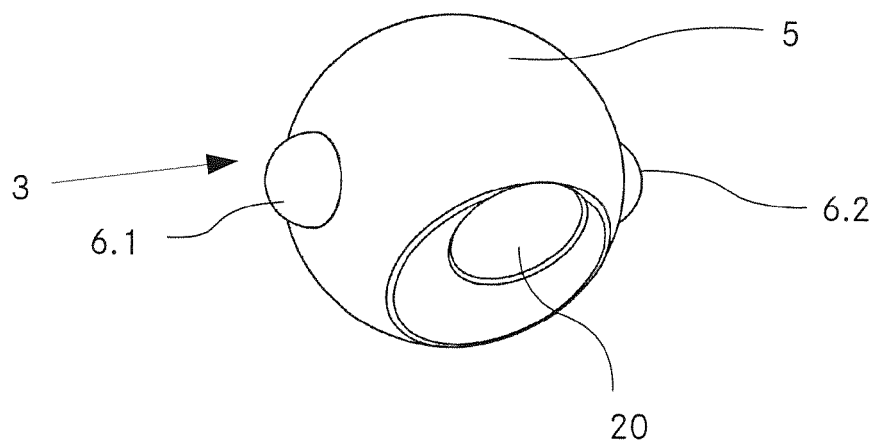
FIG. 2 a detailed view of the second element of the joint implant according to FIG. 1.

FIG. 2 shows a detailed view of the second element 3 of the joint implant 1 according to FIG. 1. The shape of the two protrusions 6.1, 6.2 as well as of the ball head may be clearly recognized in this figure. As may be seen, the ball head 5 is in the shape of a dome, i.e. of a sphere which is cut by a plane, while the two protrusions 6.1, 6.2 are in the form of hemispheres.

Figure 3:
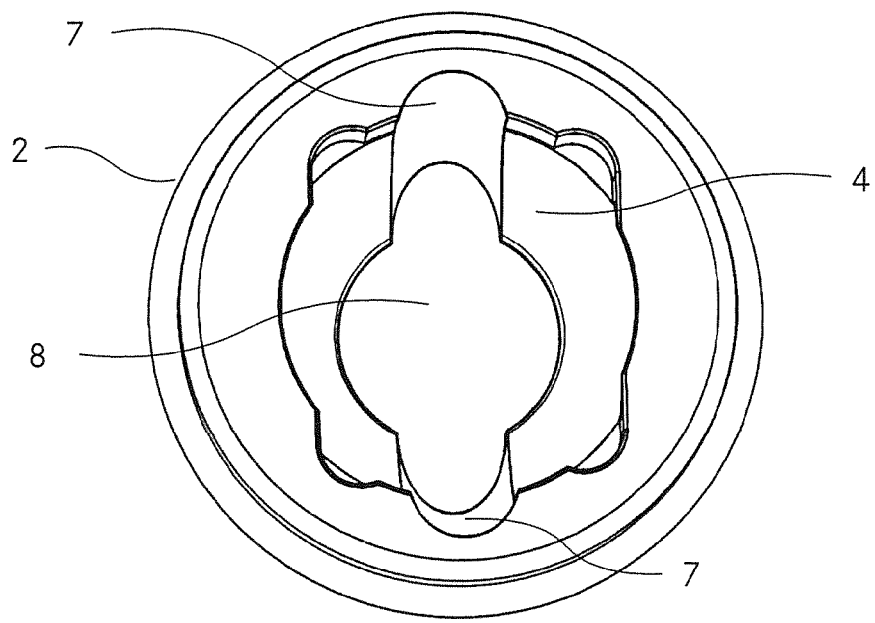
FIG. 3 a detailed view of the first element of the joint implant according to FIG. 1.

FIG. 3 shows a detailed view of the first element 2 of the joint implant 1 according to FIG. 1. As may be seen, the groove 7 has a hemispherical shape and is arranged on the hemispherical socket 4 along a great circle. The groove 7 thereby spans the socket 4 from edge to edge. Around the apex of the hemispherical socket 4, an opening 8 is provided.

Figure 4:
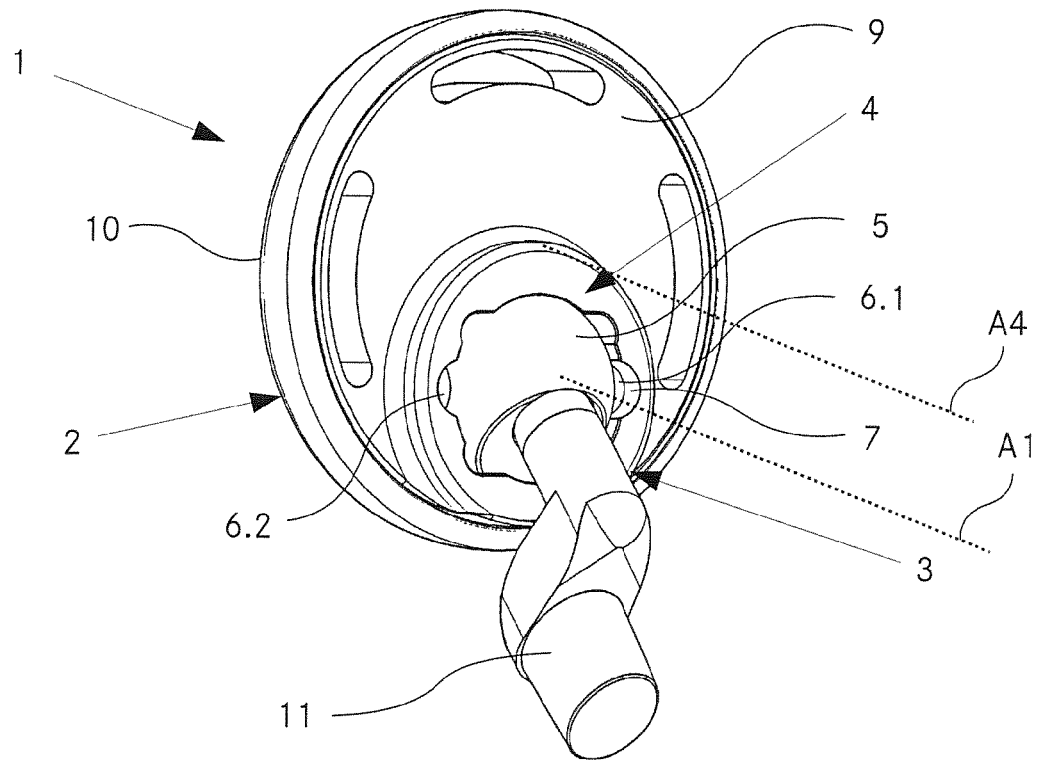
FIG. 4 an alternative embodiment of a joint implant according to the present invention.

FIG. 4 shows an alternative embodiment of a joint implant 1 according to FIG. 1. This embodiment may be used e.g. as shoulder prosthesis. The first element 2 comprises a circular inlay 9 on which the hemispherical socket 4 is located at an eccentric position. The inlay 9 is rotatably connected to a base member 10 and rotates around a fourth axis A4. The groove 7 of socket 4 is arranged in such a way that the first axis A1 around which rotational movement is prohibited by the engagement of the two protrusions 6.1, 6.2 and the groove 7 is arranged generally parallel to the fourth rotational axis A4 of the inlay 9. Hence, by the specific arrangement of the embodiment according to FIG. 4, an offset of the first rotational axis A1 is achieved. Further, the second element 3 comprises a generally Z-shaped adaptor 11 connected with the ball head 5. By means of the adaptor 11 it is possible to offset the attachment of a shaft or stem to the second element. Such an offset is particularly advantageous in connection with a shoulder prosthesis.

Figure 5:
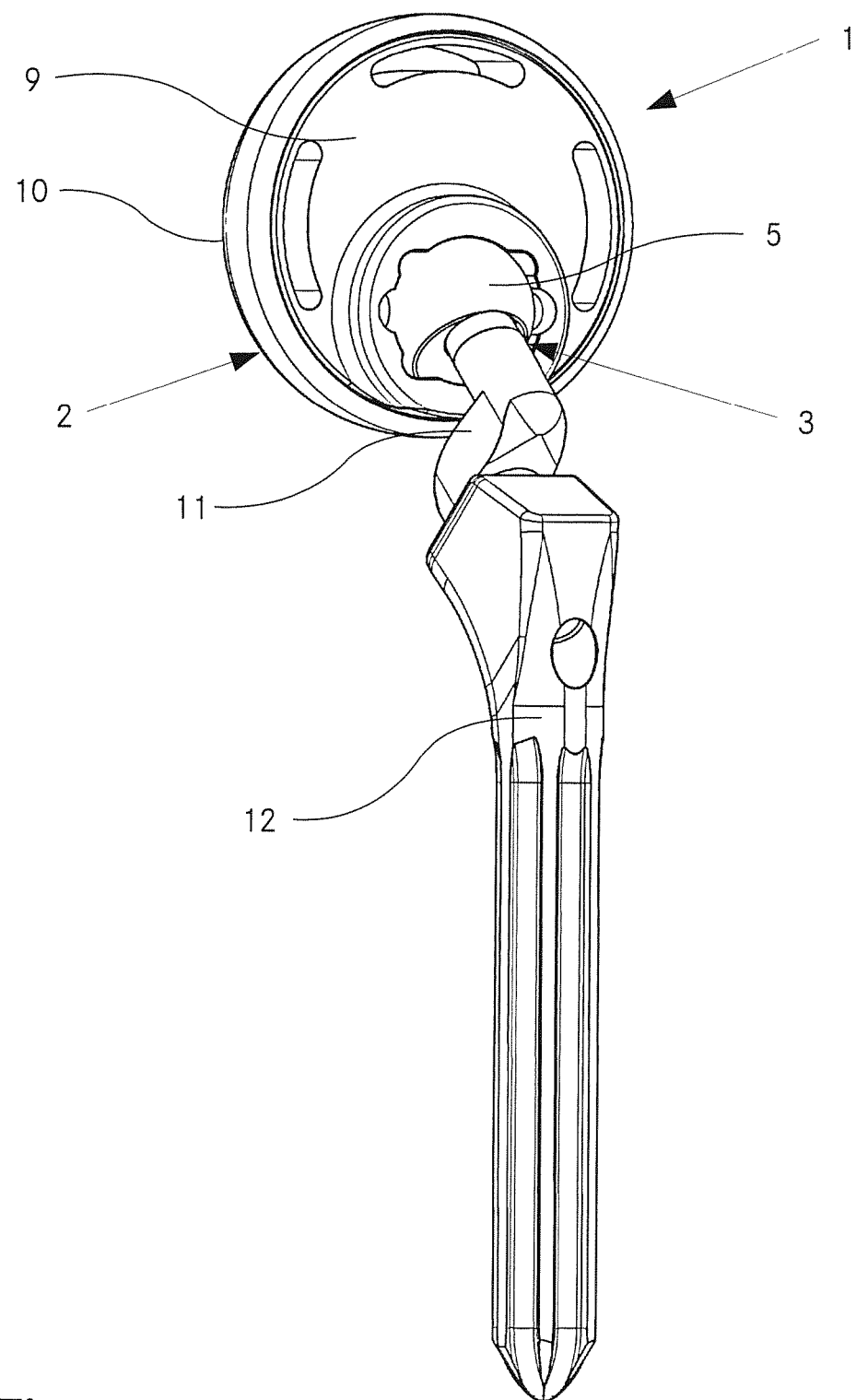
FIG. 5 the joint implant according to FIG. 4 configured as shoulder prosthesis.

FIG. 5 shows the joint implant 1 according to FIG. 4 configured as shoulder prosthesis. A shaft 12 is affixed to the adaptor 11. The shaft 12 is sized and shaped to be inserted in a humerus of a patient. The base element 10 is preferably sized and shaped to be positioned in the glenoid cavity, its outer rim engaging with the coracoid and acromial processes. Provision of a set of adaptors 11 having different configurations enables the customization of the shoulder prosthesis implant to the anatomy of different patients in a simple manner.

Figure 6:
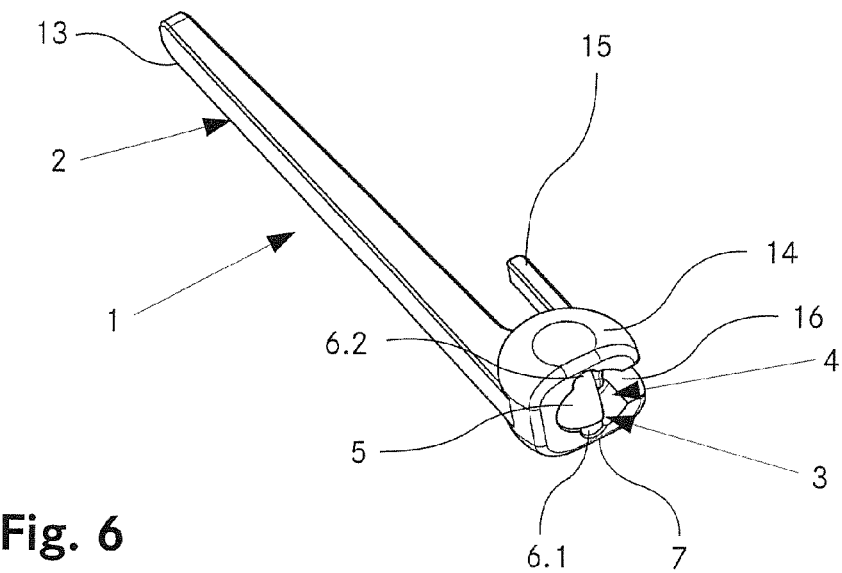
FIG. 6 an inventive joint implant configured as artificial elbow.

FIG. 6 shows the inventive joint implant 1 configured as artificial elbow. The first element 2 comprises a stem 13 sized and shaped to be implanted in the distal humerus of a patient as well as a generically hemispherical head portion 14 comprising the socket 4. An anterior support member 15 extends from the head portion 14 parallel to the stem 13, said anterior support member 15 only spanning along a short portion of the stem 13 and being intended to engage with the anterior cortex of a humeral bone. The head portion 14 includes a recess 16 intersecting the socket 4. The ball head 5 of the second element 3 of the joint implant 1 is inserted into the socket 4, whereby the groove 7 and the two protrusions 6.1, 6.2 restrict the movement of the ball head 5 within the socket 4 such that the stem 13 and an ulnar stem (shown in FIG. 7) inserted into the connection portion 20 of the second element 3 may not be moved relative to each other outside of a plane parallel to the longitudinal axis of the stem 13. This configuration allows providing a joint implant which mimics the natural freedom of movement of an elbow joint.

Figure 7:
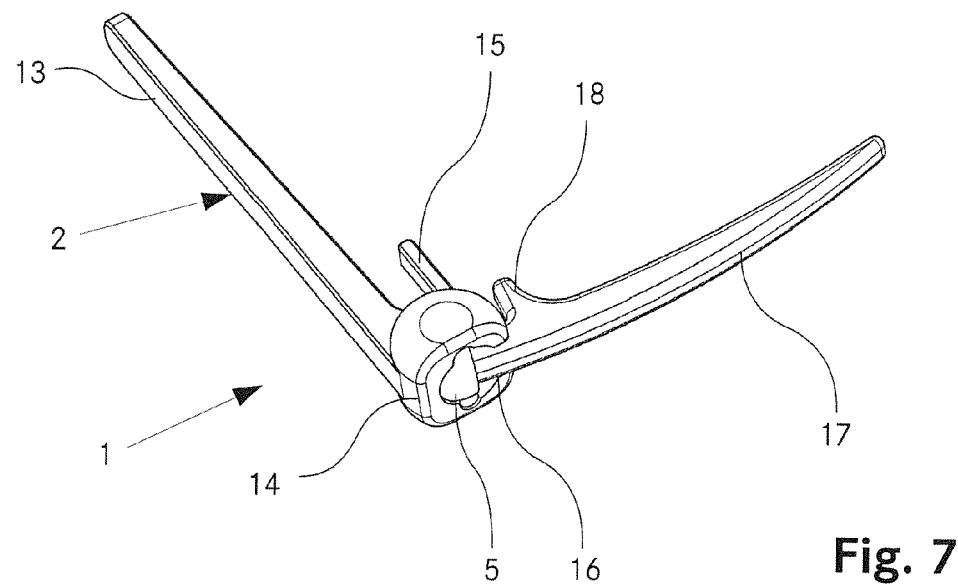
FIG. 7 the complete artificial elbow according to FIG. 6.

The complete artificial elbow is represented in FIG. 7. In addition to the elements as shown in FIG. 6, an ulnar stem 17 is attached to the ball head 5. The function of the recess 16 becomes apparent as allowing an enhanced range of motion to the ulnar stem 17 in one direction corresponding to a flexion movement of the elbow as opposed to the other direction. An additional depth stop 18 is arranged on the ulnar stem 17 which serves to limit the depth of insertion of the stem 17 into an ulnar bone.

Figure 8:
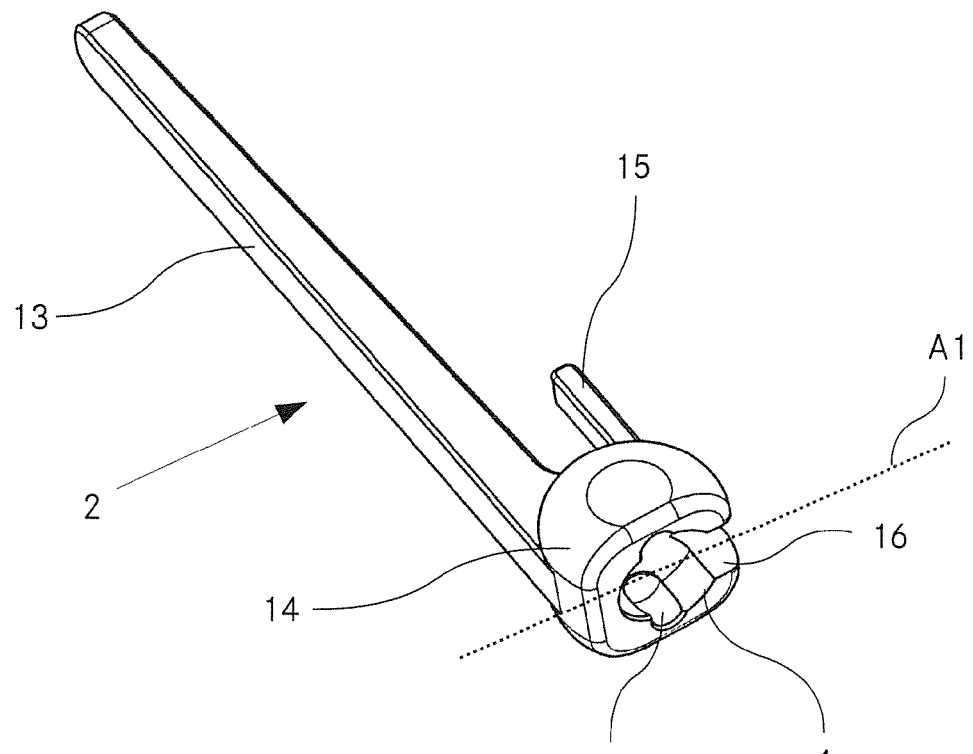
FIG. 8 the first element of the artificial elbow according to FIG. 7.

FIG. 8 shows the first element 2 of the artificial elbow in some more detail. As may be seen, the groove 7 does not span from the edge of the socket 4 to the apex, but terminates at about half the distance between the edge and the apex. This allows to additionally limiting the rotational movement of the ball head 5 within the socket 4 around the first axis A1.

Figure 9:
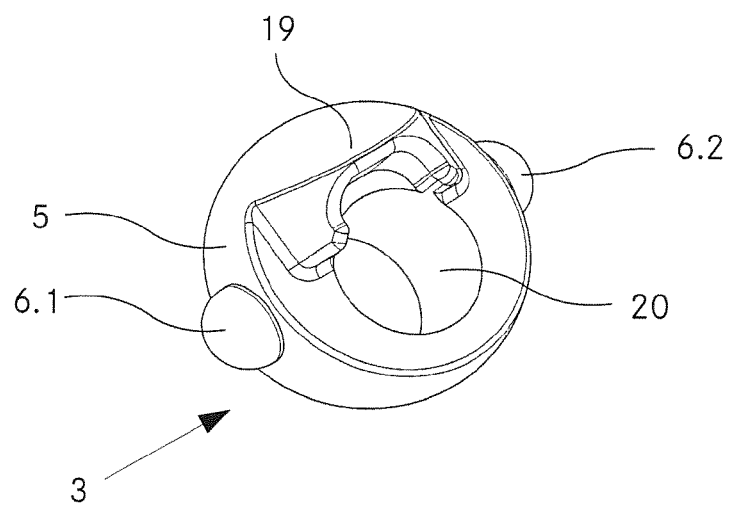
FIG. 9 the second element of the artificial elbow according to FIG. 7.

The second element 3 of the artificial elbow is shown in FIG. 9. As in the previous examples, the ball head 5 is in the shape of a dome. However, in this embodiment, the ball head 5 comprises a nose 19 protruding from the otherwise hemispherical shape. The nose 19 acts as an additional support for the ulnar stem 17 which may be attached to the ball head 5 by means of connection portion 20.

We claim:

1. An artificial joint implant comprising a first element with a socket and a second element with a ball head, said socket being at least hemispherical and said ball head being inserted in said socket such as to form a ball-and-socket connection between said first element and said second element, movement of said ball head in said socket being restricted in at least one degree of freedom by means of an at least one protrusion engaged in an at least one groove, said at least one protrusion being provided on said socket and said at least one groove being provided on said ball head or vice versa, wherein said first element further comprises an inlay rotatably coupled to a base portion around a first axis of rotation, wherein said at least one protrusion and said at least one groove are arranged to block said at least one degree of freedom of said ball-and-socket connection around a second axis of rotation which is substantially parallel to the first axis of rotation.

2. The artificial joint implant according to claim 1, wherein said at least one groove is positioned along a great circle of said ball head or of said socket.

3. The artificial joint implant according to claim 1, wherein said at least one groove has a width which is equal to or larger than a width of said at least one protrusion.

4. The artificial joint implant according to claim 1, wherein said at least one protrusion is cylindrical or hemispherical in shape.

5. The artificial joint implant according to claim 1, wherein said at least one groove is provided on said socket, wherein said at least one groove spans only a portion of the distance between a circumferential edge and an apex of said socket.

6. The artificial joint implant according to claim 1, wherein said ball head is in the form of a dome or of a spherical segment.

7. The artificial joint implant according to claim 6, wherein said at least one groove is provided on said ball head, wherein said at least one groove spans only a portion of the distance between a circumferential edge and an apex of said dome or only a portion between two circumferential edges of said spherical segment.

8. The artificial joint implant according to claim 1, wherein said at least one protrusion has a central axis which is oriented such as to intersect the center of the socket or the ball-head.

* * * * *